United States Patent
Hagele

[19]

[11] Patent Number: 6,129,248

[45] Date of Patent: Oct. 10, 2000

[54] PRECISION RELEASE TIP FOR MEDICINAL LIQUID DROPPER

[76] Inventor: James Hagele, 13262 Evergreen Dr., Nevada City, Calif. 95959

[21] Appl. No.: 09/156,216

[22] Filed: Sep. 18, 1998

[51] Int. Cl.[7] .................................................. B65D 47/18
[52] U.S. Cl. .......................... 222/420; 222/571; 604/295
[58] Field of Search .................................... 272/420, 571, 272/108; 604/295

[56] References Cited

U.S. PATENT DOCUMENTS

| | | | |
|---|---|---|---|
| 4,338,936 | 7/1982 | Nelson | 604/295 |
| 4,792,334 | 12/1988 | Py | 604/295 |
| 4,927,062 | 5/1990 | Walsh | 222/420 |
| 5,267,986 | 12/1993 | Py | 604/295 |

*Primary Examiner*—Philippe Derakshani

*Attorney, Agent, or Firm*—Heisler & Associates

[57] ABSTRACT

A tip 10 for a liquid dropper 2 is provided which allows liquids such as eye medication to be easily and precisely released from the dropper. The tip 10 is oriented in a substantially horizontal position with an opening 20 in the tip 10 located directly above the targeted area of a patient's eye E. The opening 20 is surrounded by a substantially planar annular face 30 which enhances control of the trajectory of each dispensed droplet D. The annular face 30 encourages the release of each droplet D along the plane formed by the annular face 30. A perimeter ring 40 circumscribes the annular face 30 and abuts a circumambient notch 50. The narrow width 42 of the perimeter ring 40, juxtaposed against the geometric departure of the notch 50, creates an impediment to wettable adhesion of each droplet D to an exterior surface of the tip 10 by minimizing the lateral wettable area available to a droplet D as it exits the opening 20, descends along the annular face 30, then drops toward the eye E of the patient.

18 Claims, 4 Drawing Sheets

PRECISION RELEASE TIP FOR MEDICINAL LIQUID DROPPER

FIELD OF THE INVENTION

This invention relates to dropper tips for dispensing medicinal liquids. More particularly, this invention relates to dropper tips configured to precisely instill medicinal eye drops.

BACKGROUND OF THE INVENTION

The placement of medicinal liquid in a patient's eye tends to be both difficult and annoying, particularly where the medicinal liquid is being self-administered. The process of instilling eye drops using the vast majority of eye droppers on the market today tends to be awkward at its best. First, a patient's head is substantially reclined and the eye dropper inverted over the patient's head. Next, the patient must attempt to accurately position the tip of the dropper over the appropriate portion of the eye. Then, the patient squeezes the reservoir of the eye dropper to dispense the requisite number of eye drops.

Precise application of the liquid eye drop medicine is thwarted by a lack of correspondence between the end of the tip of the eye dropper and the point at which each eye drop actually releases from the tip. If the eye dropper is held in a substantially vertical position, a drop will tend to fall toward a point immediately below the opening in the tip of the dropper. However, most people tend to use an eye dropper rotated away from a perfectly inverted position. This is especially true for elderly patients and others who have limited wrist and shoulder range of motion and have difficulty locating the dropper directly over the eye. As the eye dropper is rotated away from vertical, droplets will have a tendency to wettably adhere to the exterior surface of the tip surrounding the opening. Each subsequent droplet will tend to roll further along the tip away from the opening before dropping from the tip. Consequently, the point of release for each droplet will be somewhat offset from the location of the opening in the end of the tip. Often a portion of the liquid will be wasted as it remains adherent to the surface of the tip and refuses to fall.

Since a patient typically uses the open end of the tip of the eye dropper as a targeting mechanism, eye drop instillation efficiency and accuracy is maintained so long as droplets release from a point adjacent the opening in the tip. Once this targeting mechanism fails, dispensed eye drops will more frequently fail to reach the eye, with some drops falling only partially within the eyelid and others falling completely outside the eye.

Recognizing that a portion of the intended dosage has missed its target, a patient may elect to administer a second or even third dosage. As a result, a patient may unintentionally administer an excessive volume of medicine. This overdose could itself prove detrimental to the patient. Further, the waste will prematurely consume the supplied prescription volume, thereby shortening the duration of treatment and potentially failing to adequately treat the condition for which the medicine was prescribed.

Many persons, particularly the elderly, are not physically able to effectively self-administer medicinal eye drops using existing droppers with basic tips. They may have cervical spine or muscular problems of the neck resulting in limited head motion. Hence, these individuals would have difficulty tilting their heads sufficiently to provide an adequate target for placement of the eye drops. Additionally, patients may have wrist, shoulder or other upper body mobility problems which preclude lifting their arms sufficiently to raise the eye dropper bottle over their heads to allow the eye drops to be dispensed from a more vertical position of the dropper. Further, many individuals may experience vertigo or dizziness while attempting to dispense eye drops with their heads tilted backward. As people age, they frequently experience inner ear changes which cause them to more easily lose their balance when their head is extended. Hence, asking an elderly person to self-administer eye drops using today's standard droppers may be awkward or impossible in many situations.

The precision release tip is of great help in instilling drops into the eyes of a patient by another individual. With the current eye droppers, one must hold the bottle in a near vertical manner in front of the patient's eye. This presents a more threatening gesture to the patient and the protective reflexes of the eye cause the patient to squeeze their eyelids, thus making it difficult to instill the drops. With the precision tip dropper, the bottle may be held in a more horizontal position and below the line of vision. When this is combined with retracting the lower eyelid, a drop can be instilled without any threat to the eye.

Most standard eye droppers described in the prior art are somewhat conically-shaped with a larger base end of the tip attached to a reservoir of liquid eye medication. The free end of the tip is penetrated by an opening through which each drop of liquid eye medication is discharged. With the distal end of a standard tip directed perfectly downward, an eye drop will likely drop from the opening in the tip to fall toward a point on the patient's eye directly below the opening of the tip.

As the tip is rotated from an inverted toward a more horizontal position, liquid flowing out the opening of the standard tip will have a tendency to spread over and wettably adhere to a portion of the exterior surface of the tip. Once the exterior surface of the tip becomes wetted by the liquid medication, each drop of liquid exiting the opening in the tip will have a greater tendency to flow along the previously wetted path by virtue of molecular adhesion. The greater the wetted area of the exterior surface of the tip, the greater the tendency for each droplet to flow along the wetted surface.

As each droplet flows along the wetted surface, the point of release from the tip moves farther away from the opening in the tip. The liquid exiting the opening in the tip will flow along the wetted surface to accumulate at a point adjacent the boundary between the wetted and dry portion of the tip. As the discharged liquid flows to this boundary, sufficient mass will accumulate until a drop forms and falls from a point adjacent the boundary. Consequently, the drops no longer fall from the end of the tip. Although a patient may have the end of the prior art tip located substantially directly above the eye, the drops will likely roll down the tip to release at a point away from the end of the tip and miss the eye.

Accordingly, a need exists for an eye dropper tip capable of maintaining correspondence between the opening in the end of the tip and the point of release for each droplet to allow a patient to accurately and effectively self-administer eye drops.

SUMMARY OF THE INVENTION

The present invention is an improved tip for eye droppers used to accurately dispense and instill medicinal liquids in a targeted area adjacent or on the cornea of a patient's eye. The tip has a unique shape which maintains a consistent correspondence between the distal free end of the tip and the point from which each dispensed droplet releases to fall toward the targeted portion of a patient's eye. The tip of the present invention is integrated with an eye dropper bottle containing a reservoir of medicinal liquid. The reservoir is squeezed to dispense medicinal liquid out an opening in the distal free end of the tip.

A discharge tube provides a conduit to feed medicinal liquid from the reservoir to the opening in the tip. The opening in the tip is surrounded by a planar annular face. The annular face is circumscribed by a perimeter ring which extends substantially perpendicularly from the outer edge of the annular face. The annular face and perimeter ring form an abrupt corner at the outer edge to encourage the release of a droplet from the outer edge.

A notch in the tip is located adjacent the perimeter ring on a side of the perimeter ring opposite the annular face. This notch further encourages the release of a droplet from the perimeter ring by blocking the drop from migrating away from the distal free end of the tip. Thus configured, a patient can reliably expect to release a drop from a point on the perimeter ring of the tip, thereby increasing the accuracy of administration of the liquid eye medication to the eye and prevent a waste of drops. The notch can be formed either by cutting radially toward a central axis of the tip or by having the perimeter ring extend away from the distal free end of the tip.

OBJECTS OF THE INVENTION

A primary object of the present invention is to provide a tip for an eye dropper which substantially improves the accuracy and reliability of the application of medicinal liquids to a patient's eye.

Another object of the present invention is to provide a tip for an eye dropper which may be used without requiring patients to tilt their heads excessively backward.

Another object of the present invention is to provide a tip for an eye dropper which may be used without having to substantially elevate the dropper above the patient's head.

Another object of the present invention is to provide a tip for an eye dropper which allows a patient to keep his or her head in a more upright position during application to avoid potential dizziness and vertigo.

Another object of the present invention is to provide an eye dropper with a tip whose distal end consistently corresponds to the point of departure of each droplet from the tip.

Another object of the present invention is to provide a tip for an eye dropper which allows the dropper to be used in a horizontal, inverted or somewhat upright position.

Another object of the present invention is to provide a tip for an eye dropper which is of simple and reliable manufacture.

Other further objects of the present invention will become apparent from a careful reading of the included drawing figures, the claims and detailed description of the invention.

DESCRIPTION OF THE PREFERRED EMBODIMENT

Figures 3, 4:
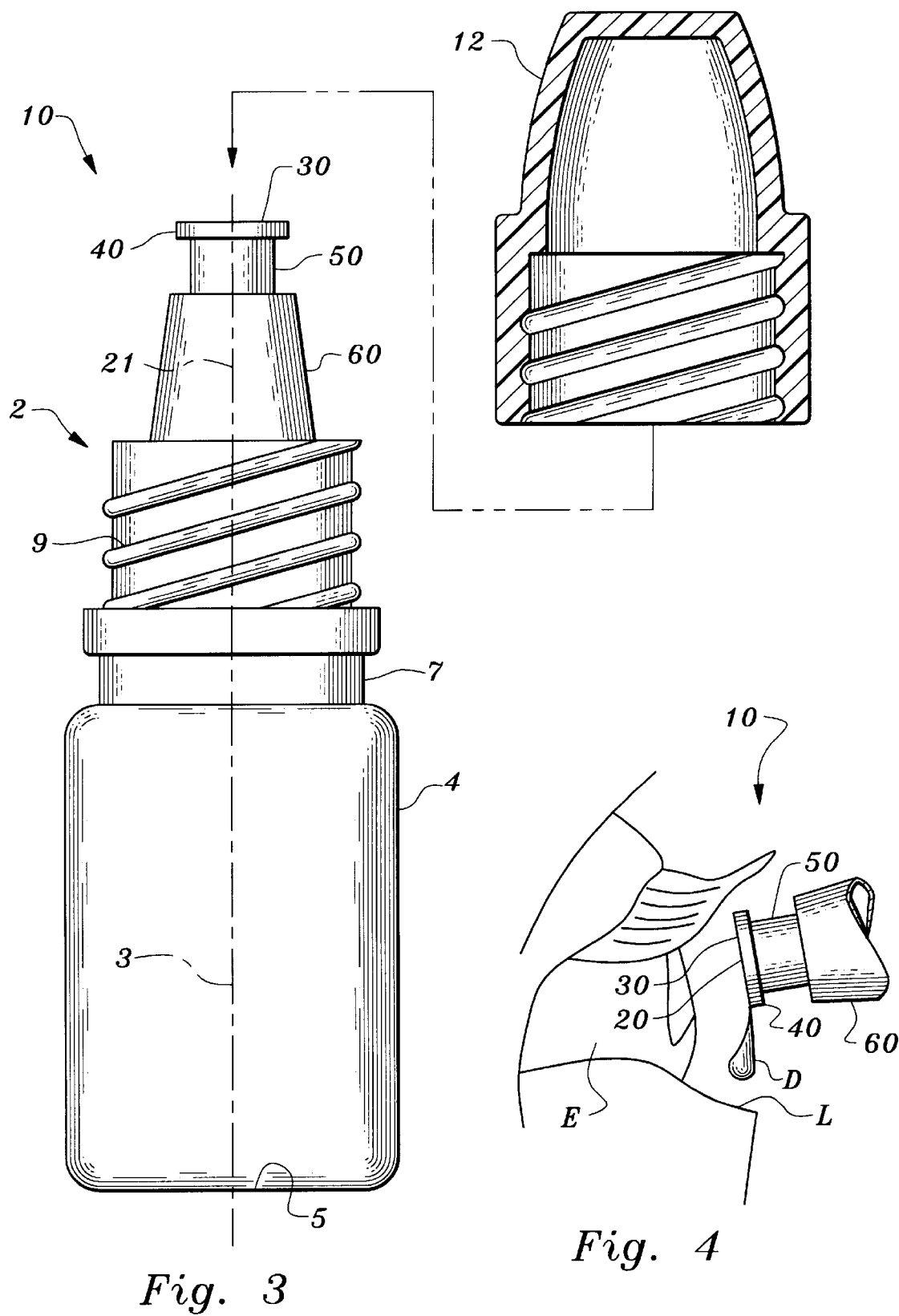
FIG. 3 is a side elevation view of a first embodiment of the tip of the present invention integrated with a standard eye dropper bottle, and showing a cap for the tip in cross-section.
FIG. 4 is a side elevation view of the first embodiment of the tip of the present invention in use, instilling a droplet of medicinal liquid in a patient's eye.

Referring to the drawings, wherein like reference numerals represent like parts throughout the various drawing figures, reference numeral 10 (FIG. 3) is directed to an eye dropper tip 10 to ease and simplify application of medicinal liquid to a patient's eye E (FIG. 4). The tip 10 allows a medicinal liquid to be accurately and reliably instilled in a patient's eye E, thereby enhancing dosage accuracy and minimizing waste of the prescribed medicine.

Figure 5:
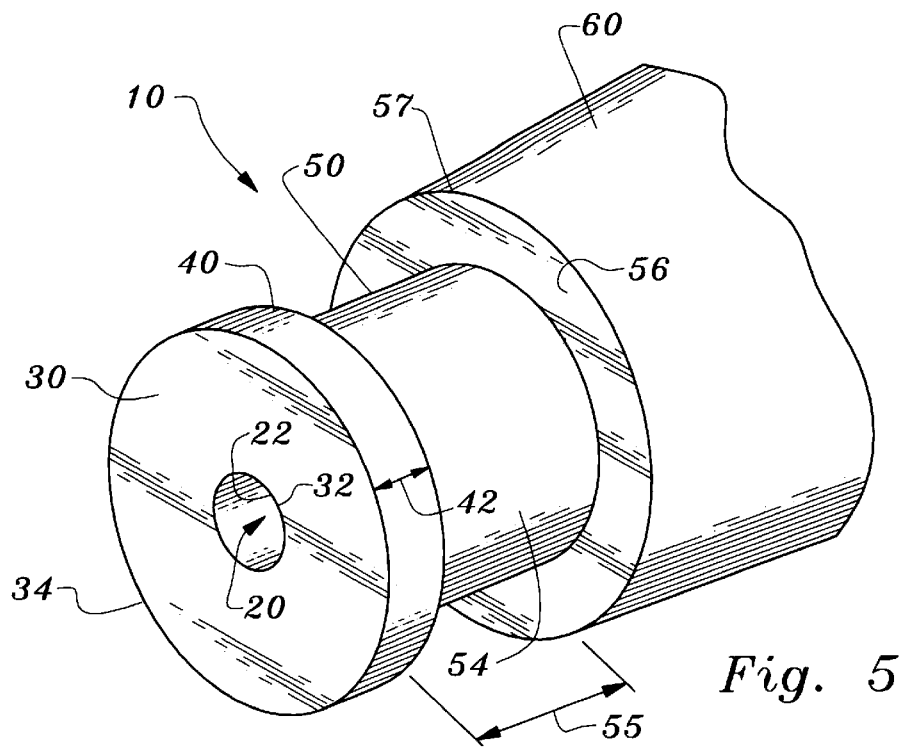
FIG. 5 is a perspective view of the first embodiment of the tip of the present invention.

In essence, and with initial reference to FIG. 5, the basic details of the tip 10 of the present invention are described. The tip 10 includes a small opening 20 (FIG. 5) through which eye drops D are discharged to fall toward the eye E of a patient (FIG. 4). A planar annular face 30 radially surrounds the opening 20 (FIG. 5). A narrow cylindrical perimeter ring 40 circumscribes the perimeter of the annular face 30. A notch 50, having an inner radius less than that of the perimeter ring 40, creates an abrupt geometric departure adjacent the perimeter ring 40. An extension surface 60, of greater diameter than the notch 50, extends rearward to join the tip 10 to a threaded portion 9 of an eye dropper bottle 2.

The tip 10 of the present invention is integrated with the dropper bottle 2 (FIG. 3). The dropper bottle 2 has a central axis 3. The dropper bottle 2 includes a deformable reservoir 4 to hold the medicinal liquid. The reservoir 4 includes a floor 5 which defines the bottom of the dropper bottle 2. At an upper end opposite the floor 5 of the dropper bottle 2, a neck 7 transitions to the threaded portion 9 of the dropper bottle 2. The threaded portion 9 of the dropper bottle 2 is sized to threadably engage a cap 12 to cover and seal the tip 10 when the dropper bottle 2 is not in use.

Figure 6:
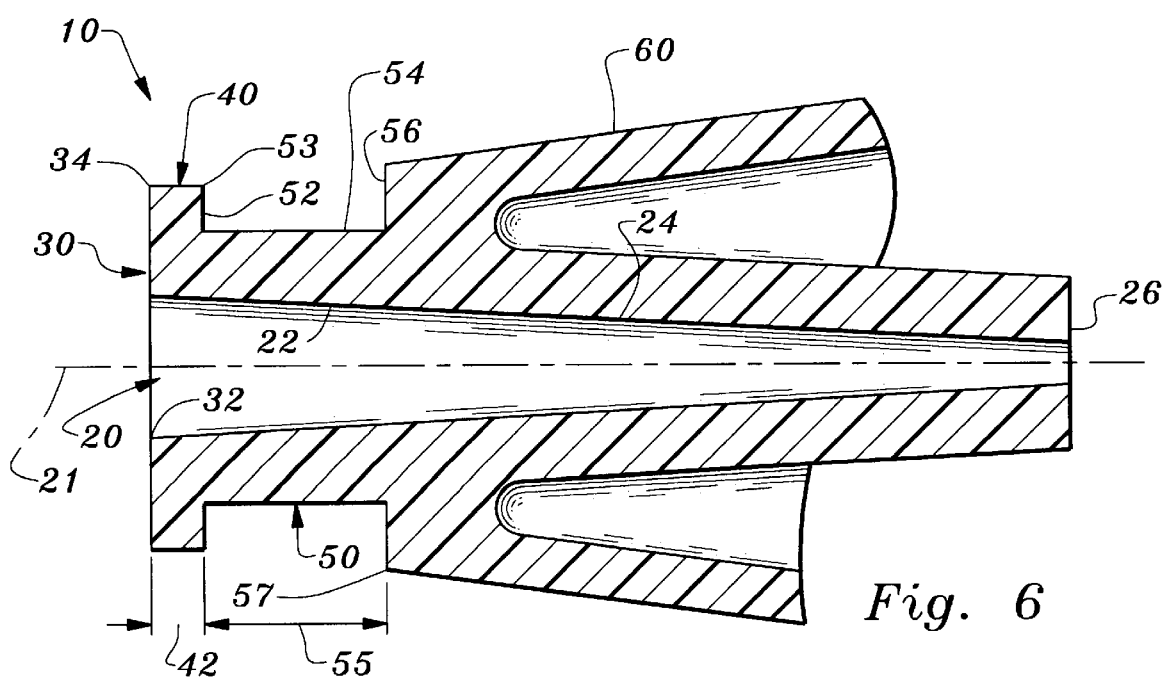
FIG. 6 is a cross-sectional view of the first embodiment of the tip of the present invention.

More specifically, and with particular reference to FIGS. 5 and 6, the details of the tip 10 of the present invention are described. The tip 10 provides a means to precisely deliver and instill liquid medicine into a patient's eye E (FIG. 4).

The tip 10 and associated dropper bottle 2 are preferably made from a resilient thermoplastic material which is compatible with injection molding techniques. The tip 10 should be sufficiently deformable to prevent injury to a patient's eye E if the tip 10 is inadvertently placed against the patient's eye E during instillation.

A circular opening 20 penetrates the distal free end of the tip 10 (FIGS. 5 and 6). The opening 20 defines a transition between an interior of the tip 10 and an exterior of the tip 10. An elongate discharge tube 22, most clearly shown in FIG. 6, provides a conduit and pathway to transfer liquid within the reservoir 4 of the dropper bottle 2 toward the opening 20 in the tip 10. The discharge tube 22 has an inner surface 24 which tapers conically and is preferably concentrically aligned with the opening 20 along a central axis 21 of the tip 10 and dropper bottle 2. The discharge tube 22 extends away from the opening 20 of the tip 10 toward the floor 5 of the reservoir 4. A fluid inlet 26 penetrates an end of the discharge tube 22 opposite the opening 20 nearest the reservoir 4 of the dropper bottle 2. Because the inlet 26 is smaller than the opening 20, fluid flow is constricted at the inlet 26 and tends to be released slowly as drops D out of the opening 20 (FIG. 4). Because the inlet 26 does not extend to the reservoir 4, the dropper 2 is lowered to allow the tip to be gravity filled and deliver liquid to the inlet 26.

An annular face 30 surrounds and extends radially from the opening 20 of the tip 10 (FIG. 5). The annular face 30 is preferably substantially planar and oriented perpendicular to the central axis 21 of the tip 10. An inner edge 32 of the annular face 30 defines the circumference of the opening 20 (FIG. 5). An outer edge 34 forms the circumference of the annular face 30 of the tip 10. As an alternative, the annular face 30 can be stepped, curved or angled as the annular face 30 extends from the inner edge 32 to the outer edge 34.

A perimeter ring 40 circumscribes and extends axially away from the outer edge 34 of the annular face 30, substantially concentric with the central axis 21 (FIGS. 5 and 6). The perimeter ring 40 is preferably cylindrically-shaped, conforming to the diameter of the outer edge 34 of the annular face 30. Alternatively, the ring 40 can be square or have a variety of other shapes. The perimeter ring 40 preferably extends perpendicularly from the annular face 30 to form an abrupt corner at the outer edge 34 of the annular face 30. The perimeter ring 40 has minimal width 42 (FIGS. 5 and 6). Experience has shown that abrupt, narrow and thin edges, especially when dry, more readily release a drop of liquid adhering thereto. The annular face 30 and narrow perimeter ring 40 cooperatively encourage release of each droplet D from the tip 10 along a trajectory vector that is substantially aligned with the planar surface formed by the annular face 30 of the tip 10.

A notch 50 is located adjacent to the perimeter ring 40 of the tip 10 and on a side of the perimeter ring 40 opposite the annular face 30 (FIGS. 3 and 5). The notch 50 is preferably circumambient about the tip 10 to form a barrier to minimize the probability for discharged medicinal liquid to flow from the opening 20 along the tip 10 toward the exterior surface 60. Alternatively, the notch 50 can be only on a lower side of the tip 10. The notch 50 has a cylindrical surface 54 (FIG. 6) with a diameter somewhat less than the diameter of the perimeter ring 40. A front wall 52 of the notch 50 extends radially inward from a front rim 53 of the notch 50 adjacent the perimeter ring 40. The notch 50 has a radial depth at least a fourth of the radius of the perimeter ring 40 The planar surface formed by the front wall 52 of the notch is preferably substantially perpendicular to the central axis 21 of the tip 10 and hence, the perimeter ring 40. The cylindrical surface 54 extends perpendicularly from the front wall 52 of the notch 50 toward an extension surface 60 of the tip 10 which extends toward the dropper bottle 2. The cylindrical surface 54 extends to abut a rear wall 56 of the notch 50. The rear wall 56 extends radially outward from the cylindrical surface 54 to form a rear rim 57. The rear wall 56 of the notch 50 intersects with the extension surface 60 to form an abrupt corner at the rear rim 57.

The extension surface 60 extends away from the rear rim 57 (FIG. 6) of the notch 50 to join the tip 10 to the threaded portion 9 of the dropper bottle 2 (FIG. 3). The extension surface 60 joins and integrates the tip 10 with the dropper bottle 2, thereby providing access to liquid medicine stored in the reservoir 4 of the dropper bottle 2. The extension surface 60 (FIG. 3) provides one form of a means to attach the tip 10 to the reservoir 4 of the dropper 2. Other attachment means could alternatively be used, such as a flexible plastic tube. As most clearly shown in FIG. 3, the extension surface 60 typically has a frustoconical shape. Preferably, the extension surface 60 is joined to the bottle 2 in a removable manner by friction fitting the extension surface 60 into a mating recess formed in the bottle 2.

As most clearly shown in FIG. 4, in use and operation, to instill eye drops D in a patient's eye E, the dropper bottle 2 is rotated to a more horizontal position with the opening 20 of the tip 10 placed in an aligned position directly above the desired target area of the patient's eye E.

Once the opening 20 of the tip 10 is aligned above the desired target area of the eye E, the patient or assisting person may squeeze the dropper bottle 2 (FIG. 3) to compress the reservoir 4 and cause the medicinal liquid to flow into the inlet 26 (FIG. 6) of the discharge tube 22 and on toward the opening 20 in the tip 10.

As the medicinal liquid accumulates within the inner tapered region 24 of the discharge tube 22, a droplet D will begin to form at the opening 20 of the tip 10. Once the droplet D reaches sufficient mass, the capillary pressure causing the droplet D to remain within the discharge tube 22 will be overcome, allowing the droplet D to exit out the opening 20 in the tip 10.

Once the droplet D exits the opening 20 of the tip 10, the droplet D will "roll" downward along the annular face 30 of the tip 10 (FIG. 4). As the droplet D reaches the perimeter ring 40 of the tip, a portion of the droplet D will begin to extend past the outer edge 34 of the annular face 30. As more of the droplet D extends past the outer edge 34 of the annular face 30, the wettable adhesion of the droplet D to the annular face 30 of the tip 10 will eventually be overcome by gravitational forces acting on and pulling the mass of the droplet D downward. The droplet D will then fall toward an area of the patient's eye E directly below the opening 20 of the tip 10.

The wettable adhesion of a portion of the droplet D to the annular face 30 of the tip 10 may cause a portion of the droplet D to also "roll" rearward along the surface of the perimeter ring 40 away from the opening 20 in the tip 10. In the tip 10 of the present invention, the droplet D will cease to roll back along the tip 10 once the perimeter ring 40 of the tip 10 is encountered. The width 42 of the perimeter ring 40 is narrow to minimize the rearward distance a droplet D may travel before releasing from the tip 10. Hence, each droplet D will follow a trajectory toward the targeted area on the patient's eye E where the origin of the trajectory is constrained to a point within the width 42 of the perimeter ring 40.

Consequently, the medicinal liquid may be precisely instilled into a patient's eye E at the desired location using the opening 20 and annular face 30 of the tip 10 as a reliable targeting mechanism. The tendency for each droplet D to wettably roll along the tip 10 is minimized by the narrowness of the width 42 of the perimeter ring 40 juxtaposed against the substantial gap width 55 of the notch 50. In effect, a droplet D would have to leap across the notch 50 from the perimeter ring 40 to reach the extension surface 60 to roll further along the tip 10 away from the opening 20. Even when the notch has liquid adhering therein, the notch is sufficiently deep radially and long axially to discourage migration of the droplet D past the notch 50. Hence, the tip 10 of the present invention constrains a droplet D to release at a point on the perimeter ring 40 (FIG. 4).

Figure 7:
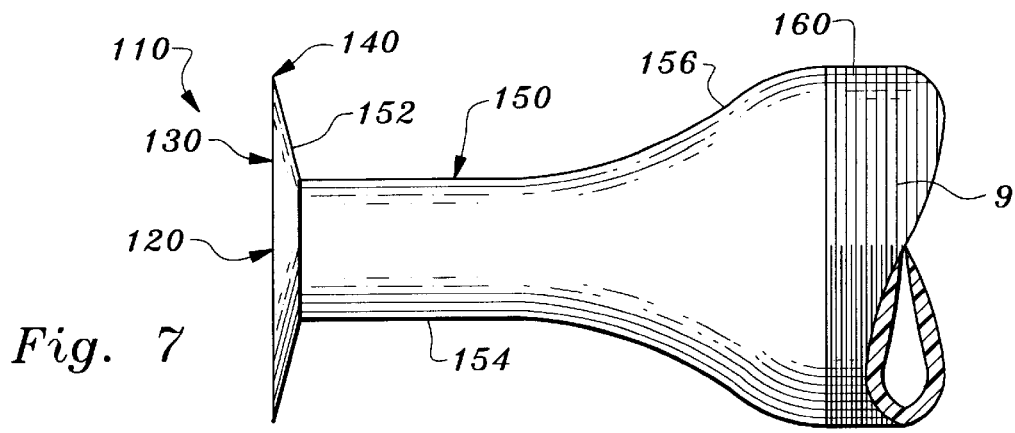
FIG. 7 is a side elevation view of a first alternative embodiment of the tip of the present invention.

With specific reference to FIG. 7, a first alternative embodiment of the tip 110 includes an opening 120 at a distal end of the tip 110 similar to the opening 20 of the preferred embodiment. A planar annular face 130 surrounds the opening 120 to provide a planar surface to govern the release and origin of the trajectory of a discharged droplet D. The annular face 130 extends to form a perimeter edge 140 with minimal thickness, thereby creating a thin edge which further narrows the range along the length of the tip 10 from which a droplet D may originate. A gap 150, having substantially less radius than the perimeter edge 140, reduces the possibility of a discharged droplet D wettably adhering to the outer surface of the tip 10. The gap 150 complements the tendency of the perimeter edge 140 to encourage release of a droplet D from the perimeter edge, thereby minimizing the potential for a droplet D to flow rearward along the tip 110. Thus, the droplet D is more likely to drop toward the intended point on a patient's eye.

The gap 150 includes a flared front surface 152 which extends radially to join the perimeter edge 140 about the annular face 130 of the tip 110. A cylindrical neck 154 of the gap 150 extends away from the opening 120 to form a barrier to wettable adhesion of each drop element complementary to the function of the perimeter edge 140. The cylindrical neck 154 merges to form a rear radial slope 156. The rear slope 156 extends to abut an extension surface 160 to join the tip 110 to a dropper bottle 2.

Figure 1:
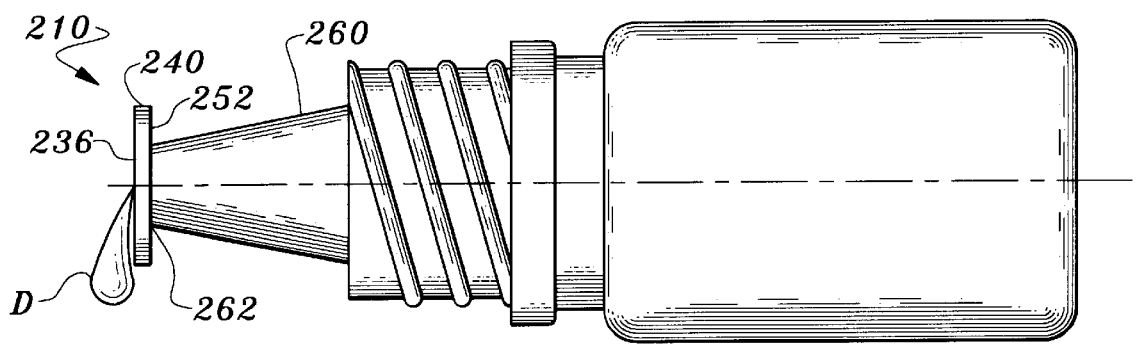
FIG. 1 is a side elevation view of a most preferred embodiment of the tip of the present invention integrated with a standard eye dropper bottle.
Figure 2:
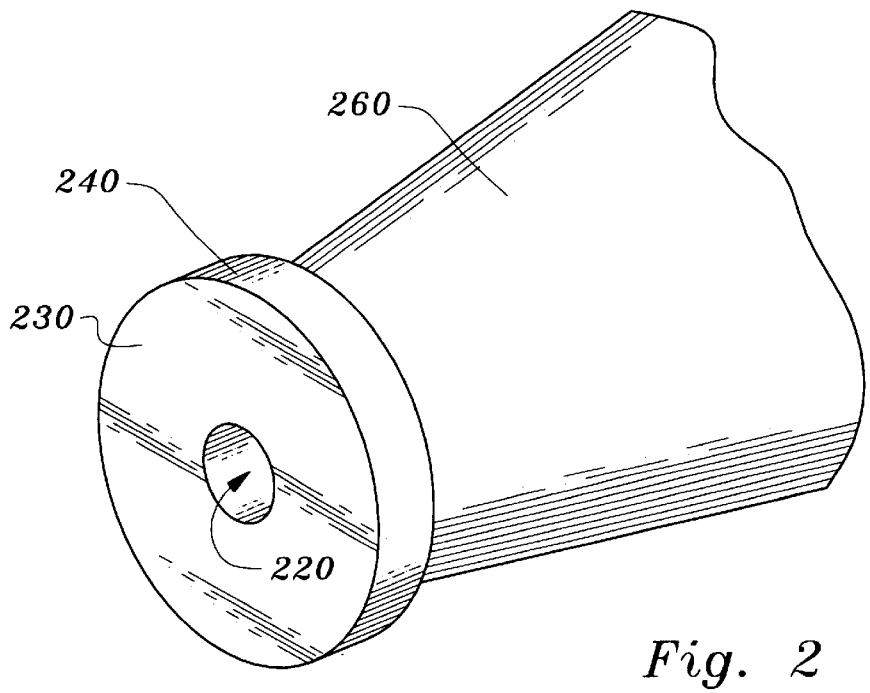
FIG. 2 is a perspective view of the most preferred embodiment of the tip of the present invention.

A most preferred embodiment of the tip 210 is illustrated in FIGS. 1 and 2. This version of the tip 210 has a simpler "notchless" configuration. A frustoconical extension surface 260 includes a terminal end 262 which abuts a rear face 252 of the tip 210. The rear face 252 extends radially away from the extension surface 260 to form an abrupt corner at the intersection of the rear face 252 and the extension surface 260 which will tend to discourage dispensed droplets D from rolling rearward along the extension surface 260. Other elements and operation of the tip 210 are similar to those of the previously described tips 10, 110.

An annular face 230 of the tip 210 (FIG. 2) includes an opening 220 at its center. The annular face 230 extends radially away from the opening 220. A circumferential perimeter ring 240 wraps about the periphery of the annular face 230, forming an abrupt corner at the intersection of the annular face 230 and perimeter ring 240. The perimeter ring 240 extends substantially perpendicularly to the annular face 230 between the annular face 230 and the rear face 252.

One important feature shared by each of these embodiments of tips 10, 110, 210 is that a perimeter contour of the tip 10, 110, 210 at least on the undersurface progresses from the opening 20, 120, 220 downward and then progresses upward again when the tip is oriented with the central axis 21 (FIG. 6) oriented close to horizontal. This local minimum elevation in the contour provides a location where drops tend to cease migration away from the opening 10, 110, 210 and grow until large enough to fall from the tip 10, 110, 210. The local minimum elevation is at least formed on the underside of the tip 10, 110, 210 and preferably circumscribes the tip 10, 110, 210 so that the tip 10, 110, 210 can be substantially radially symmetrical about the central axis 21 (FIG. 6).

Figure 8:
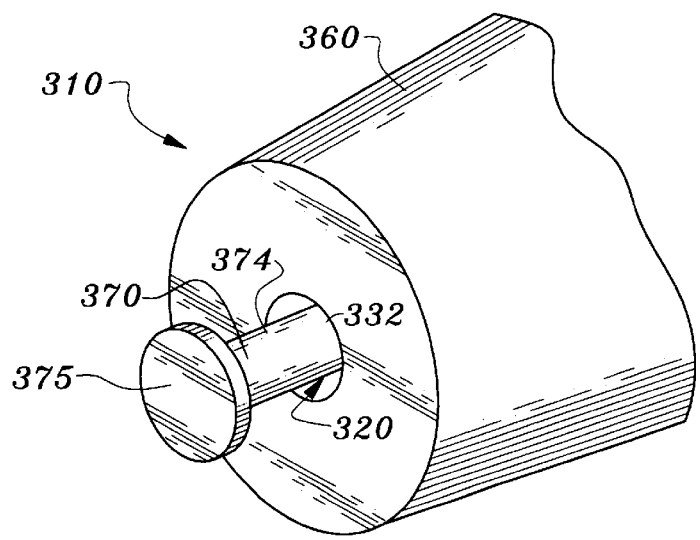
FIG. 8 is a perspective view of a further alternative embodiment of the tip of the present invention.
Figure 9:
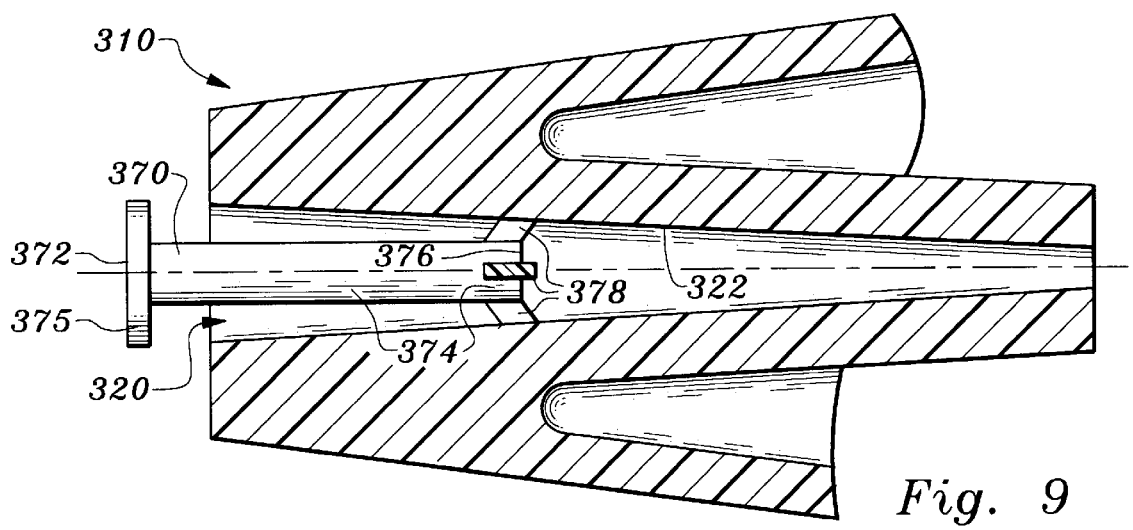
FIG. 9 is a cross-sectional view of the further alternative embodiment of the tip of the present invention.

A further alternative embodiment of the tip 310 is illustrated in FIGS. 8 and 9. The tip 310 includes a protruding central post 370 which is concentrically aligned within the discharge tube 322 of the tip 310. The central post 370 provides one form of a means to further encourage droplets D of medicinal liquid to release from a point immediately adjacent an opening 320 in the tip 310. Other similar means might include a hollow thin cylindrical wall which surrounds the opening 320 and extends away from the rim 332 of the opening 320 in the tip 310 such that liquid exits through the hollow thin cylindrical wall.

The central post 370 can be centrally affixed within the discharge tube 322 via several legs 378 extending from an inner end 376 of the central post 370. The central post 370 extends from within the discharge tube 322 of the tip 310 to protrude out the opening 320 in the tip 310. The central post 370 extends from its inner end 376 within the discharge tube 322 to terminate at a free end 372. The free end 372 of the post 370 preferably includes an annular plate 375 to blunt the free end 372 somewhat and provide another edge to direct drops from the tip 310. The central post 370 includes a cylindrical side wall 374. The central post 370 extends sufficiently past an annular face 330 of the tip 310 to provide sufficient surface area for each dispensed droplet D to preferably wettably adhere to the exterior cylindrical wall 374 of the central post 370. Additionally, the central post 370 has a width less than that of the opening 320 to allow droplets D to easily exit out the end of the tip 310, between the side wall 374 of the post 370 and a rim 332 about the opening 320.

In use and operation, medicinal liquid will flow through the discharge tube 322 of the tip 310 and about the central post 370 to exit out the opening 320. A droplet D exiting the opening 320 in the tip 310 will have a tendency to wettably adhere to the protruding portion of the cylindrical walls 374 of the central post 370. Thus, a droplet D will tend to form and release nearer the protruding free end 372 of the central post 370, thereby minimizing the tendency for a droplet D to roll rearward along the extension surface 360 of the tip 310.

Although shown in FIGS. 8 and 9 in use with a tip 310 having neither a notch nor a radially-extended annular face, the central post 370 could be combined with the three previously described tips 10, 110, 210 to further enhance correspondence between the end of each tip 10, 110, 210 and the point from which a droplet D is released.

Thus, the described embodiments of the tip 10, 110, 210, 310 will provide means by which the tips 10, 110, 210, 310 may be oriented near horizontal and still allow precise instillation of medicinal liquid in a patient's eye E. Various dropper bottle 2 designs may be used with the tips 10, 110, 210, 310 to allow a patient to accurately instill the medicinal liquid with their head in a less retracted position.

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure. When structures are identified as a means to perform a function, the identification is intended to include all structures which can perform the function specified.

What is claimed is:

1. A tip for a liquid dropper, the tip encouraging release of a drop of liquid only from a terminal free end of the tip, the tip comprising in combination:

an opening defining a transition between an interior of said tip and an exterior of said tip, said opening located at said terminal free end of said tip opposite a base of said tip, a central axis of said tip passing through said opening;

a liquid pathway leading to a liquid source, said pathway located in said interior of said tip, said pathway extending to said opening;

a perimeter surface surrounding said opening, said perimeter surface located a distance further radially away from said central axis than portions of said tip adjacent said perimeter surface, such that said perimeter surface defines a localized minimum elevation portion of said tip when said central axis of said tip is oriented near horizontal; and said perimeter surface located at least as far from said base as said opening.

2. The tip of claim 1 wherein said perimeter surface is configured as a ring oriented in a plane perpendicular to a central axis of said tip passing through said opening.

3. The tip of claim 1 wherein said perimeter ring is located the same distance from said base as said opening.

4. The tip of claim 3 wherein a notch is located on a side of said perimeter surface opposite said opening, said notch defining a region extending less radially relative to said opening than said perimeter surface.

5. The tip of claim 4 wherein said notch is located adjacent said perimeter ring, said notch completely circumscribing said tip.

6. The tip of claim 5 wherein a transition between said notch and said perimeter ring is an abrupt edge.

7. The tip of claim 3 wherein said perimeter ring has a surface area which is smaller than a size necessary to hold a drop of liquid, the drop size determined by characteristics of a saline solution in standard atmospheric conditions.

8. The tip of claim 3 wherein an annular surface extends between said opening and said perimeter ring, said annular surface oriented substantially perpendicular to said central axis.

9. A tip for a liquid dropper featuring precise targeting of discharge when a central axis of said tip is oriented close to horizontal, said tip comprising in combination:

an opening defining a transition between an interior of said tip and an exterior of said tip, said opening located at a distal free end of said tip;

said tip having a base spaced from said distal free end, said base attachable to a liquid reservoir;

a liquid pathway within said interior of said tip extending between said opening and the liquid reservoir;

said opening aligned with a central axis of said tip;

an annular surface extending substantially radially from said central axis adjacent said opening, said annular surface terminating at a perimeter ring, said perimeter ring located at least as far anteriorly from said base as said opening; and a notch located on a side of said perimeter ring opposite said annular surface, said notch extending in toward said central axis from said perimeter ring.

10. The tip of claim 9 wherein said notch has a width, extending away from said perimeter ring and parallel to said central axis, of at least two millimeters.

11. The tip of claim 9 wherein a radial depth of said notch extending in toward said central axis from said perimeter ring is at least a fourth of a radial distance said perimeter ring extends from said opening.

12. The tip of claim 9 wherein said notch completely circumscribes said tip and wherein said perimeter ring completely circumscribes said tip.

13. The tip of claim 12 wherein a transition between said front wall of said notch and said perimeter ring is an abrupt corner.

14. An eye dropper which can instill liquid eye medication into a patient's eye without requiring orientation of a tip of the eye dropper pointing below horizontal, the eye dropper comprising in combination:

a reservoir;

a tip, said tip having an opening at a front thereof and a liquid pathway therein extending between said opening and said reservoir said tip having a central axis extending through said opening;

said tip having an exterior surface extending rearward away from said opening; and a perimeter surface defining a minimum elevation in said exterior surface when said central axis is located closer to horizontal than to vertical, by extending laterally down from portions of said exterior surface adjacent said perimeter surface, said perimeter surface located at least as far anteriorly from said reservoir as said opening.

15. The eye dropper of claim 14 wherein said perimeter ring is located directly adjacent said opening.

16. A dropper tip that enables a drop of liquid to fall precisely and consistently into an eye from the terminal free end when the dropper tip is held in a horizontal orientation, rather than adhere to and migrate posteriorly along an external surface of the tip, the dropper tip comprising in combination:

a base opposite said terminal free end of said dropper tip for attachment to a liquid reservoir;

an internal passage through said dropper tip for the liquid to flow from said reservoir through said tip;

said dropper tip having an external opening at said terminal free end of said internal passage; and said dropper tip having a perimeter ring located at least as far anteriorly from said base as said external opening.

17. The dropper tip of claim 16 wherein said perimeter ring encircles said external opening of said dropper tip.

18. The dropper tip of claim 16 wherein said perimeter ring is located directly adjacent to said external opening of said dropper tip.

* * * * *